United States Patent [19]

Goins

[11] Patent Number: 4,640,269
[45] Date of Patent: Feb. 3, 1987

[54] BACK BRACE HAVING STRAP WITH WIDENED MIDDLE PORTION FOR PAD

[76] Inventor: Joan Goins, R.R. #6, Box 92, North Vernon, Ind. 47265

[21] Appl. No.: 635,834

[22] Filed: Jul. 30, 1984

[51] Int. Cl.$^4$ .............................................. A61F 5/01
[52] U.S. Cl. ............................... 128/78; 128/DIG. 15
[58] Field of Search ......... 128/78, 133, 134, DIG. 15; 2/323, 338; 224/163, 164, 165, 264

[56] References Cited

U.S. PATENT DOCUMENTS

| | | | |
|---|---|---|---|
| 1,903,081 | 3/1933 | Wotherspoon | 2/338 |
| 2,359,148 | 9/1944 | Partridge | 224/164 |
| 2,498,077 | 2/1950 | Goldberg | 2/338 |
| 3,561,434 | 2/1971 | Kilbey | 128/78 |
| 4,173,973 | 11/1979 | Hendricks | 128/78 |
| 4,202,327 | 5/1980 | Glancy | 128/78 |

FOREIGN PATENT DOCUMENTS

| | | | |
|---|---|---|---|
| 1185998 | 2/1959 | France | 224/164 |
| 693270 | 6/1953 | United Kingdom | 128/78 |

Primary Examiner—Edgar S. Burr
Assistant Examiner—Tonya Eckstine
Attorney, Agent, or Firm—Woodard, Weikart, Emhardt & Naughton

[57] ABSTRACT

An improved back brace strap is shown in combination with a back brace which has a generally cruciform shaped anterior frame having a vertical member which crosses and is fixed to a horizontal member. The back brace is configured to be applied to the anterior thoracic area of a person. Also included in the back brace is a back pad curved to conform to the shape of the lumbar area of the back. The ends of the back brace strap are reeved through slots in the back pad and are attached to the sides of the anterior frame. The back brace strap includes a central core of cotton canvas and overlying layers of absorbent terry cloth, all secured together by alternating diagonal stitching for substantially the full width of the back brace strap. The back brace strap is also provided with a widened middle portion which is wider than the length of the slots in the back pad and thereby prevents the back brace strap from being displaced longitudinally with respect to the back pad, and which also stiffens the strap in the middle to resist buckling. Velcro hook and loop type fasteners are provided near the ends the strap for length and tension adjustment.

5 Claims, 3 Drawing Figures

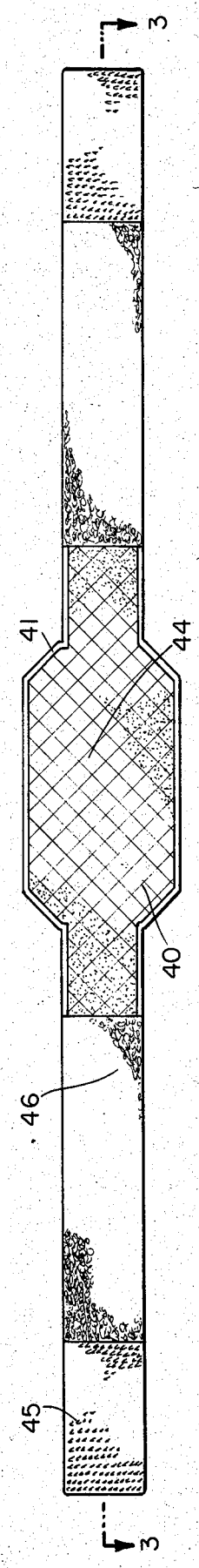
Fig.2
Fig.3

BACK BRACE HAVING STRAP WITH WIDENED MIDDLE PORTION FOR PAD

BACKGROUND OF THE INVENTION

1. Field of the Invention

This invention relates in general to back (spinal) braces and in particular to such back braces as employ strap means for applying tension between an anterior frame and a back pad.

2. Description of the Prior Art

Various types of back braces are known which have as their fundamental characteristic the application of tension between an anterior frame and a back pad. The anterior frame of such braces is configured to be applied to the anterior thoracic area of a person and is padded where it contacts the body. The back pad is connected to the left and right sides of the anterior frame by one or more straps which are adjustable to provide a suitable degree of tension, whereby the back pad applied pressure to a selected area of the spine for support and relief of pain.

An example of a prior back brace of the type discussed above is shown in U.S. Pat. No. 4,173,973, issued to Hendricks on Nov. 13, 1979. Hendricks shows a cruciform shaped anterior frame having pads mounted at the ends of each of the arms, including sternal, pubic and two side pads, with the pads being shaped to conform to the area of the body which they contact. The length of each arm is adjustible to accomodate different sized persons.

The Hendricks back pad has left and right wings having corresponding left and right slots therethrough. A right strap is reeved through the right slot of the back pad with both ends of the strap being connected to the right side pad by means of apertures in the strap which fit over a stud on the side pad. Multiple apertures spaced lengthwise on the strap permit adjustment of the length of the strap. A similar left strap is provided for connecting the left slot of the back pad to the left side pad.

A difficulty with a Hendricks type strap arrangement is that the separate looped straps provide little vertical support for the back pad when the straps are not under tension. This makes it difficult for the patient to properly position the back pad as he is putting on the brace and tightening the straps. Lack of vertical support also allows the pad to slip downward out of its proper position whenever tension on the straps is temporarily relieved, as when the patient moves.

There is a known variation of the Hendricks strap which is a single piece strap of a woven material reeved through both slots of the back pad and having opposite ends of the strap attached to the left and right side pads respectively. The means for attaching the strap to the side pads may also involve reeving the strap end through a slot in the side pad, folding the strap back on itself, and securing the strap end to the main portion of the strap with Velcro multiple hook and loop type fasteners. This type of strap provides more vertical support for the back pad than does the Hendricks strap because its one piece construction better resists buckling under the weight of the back bad. However, because this type strap is of constant width, the back pad can slip horizontally with respect to the strap, thereby moving out of its proper position.

It would be an improvement to provide a strap for use with a back brace having a back pad which would provide vertical support for the back pad and would prevent horizontal movement of the back pad when it is being worn.

SUMMARY OF THE INVENTION

According to one embodiment of the present invention, an improved back brace strap is combined with a back brace of the type having an anterior frame configured to be applied to the anterior thoracic area of a person and having a back pad configured to be applied to the lumbar area of a person. The back brace also has strap means connected to said back pad and to said anterior frame for providing suitable tension therebetween. The back pad has vertical slots for receiving the strap means therethrough. The improvement comprises a strap constructed of a cloth-like material and having a middle portion, wherein the middle portion has a width dimension greater than the length dimension of either of the back pad slots. The strap has end portions disposed through the respective slots of the back pad and secured to said anterior frame, whereby longitudinal displacement of the back pad with respect to the strap is precluded by the middle portion.

One object of the present invention is to provide a back brace having an improved back brace strap.

Related objects and advantages of the present invention will become apparent from the following description.

BRIEF DESCRIPTION OF THE DRAWINGS

FIG. 2 is an elevation view of the back brace strap of FIG. 1, shown extended flat.

FIG. 3 is a cross section view of the back brace strap of FIG. 1, taken substantially along the plane 3—3 of FIG. 2.

DESCRIPTION OF THE PREFERRED EMBODIMENT

Figure 1:
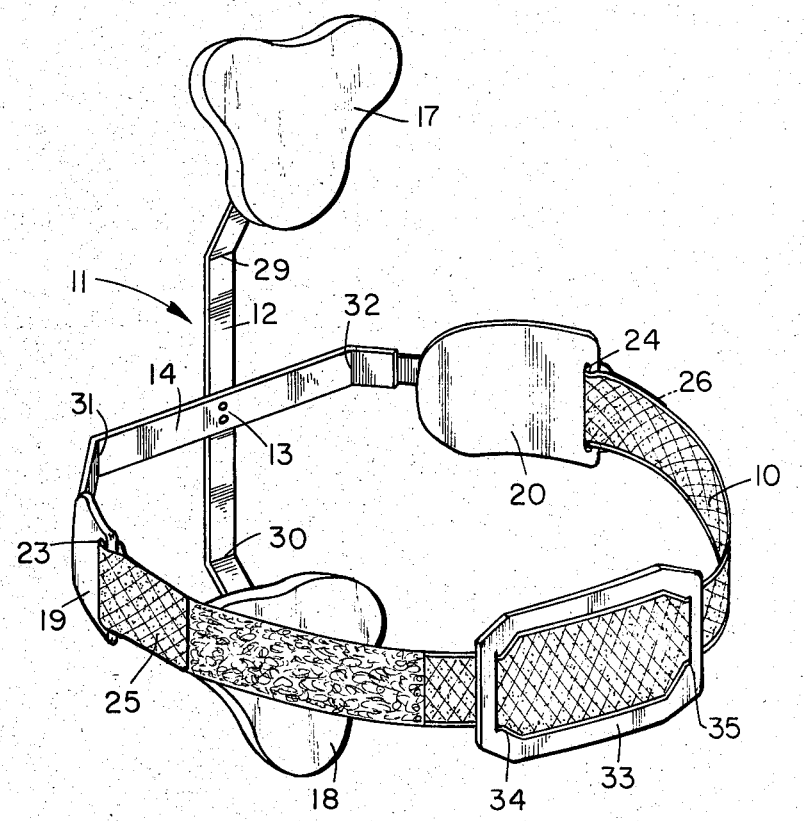
FIG. 1 is a perspective view of a back brace in combination with an improved back brace strap.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1, there is illustrated the preferred embodiment of the improved back brace strap 10 of the present invention in combination with a back brace 11.

Back brace 11 is generally cruciform shaped having a vertical member 12 which crosses and is fixed at point 13 to a horizontal member 14 such that the two members are maintained at a right angle relative to each other. Each of the ends of vertical member 12 and horizontal member 14 are terminated in a pad, including sternum pad 17, pubic pad 18, and side pads 19 and 20. Back brace 11 is configured to be applied to the anterior thoracic area of a person, with sternum pad 17 contacting the sternal area and pubic pad 18 bearing upon the pubic area. Side pads 19 and 20 are provided with vertical slots 23 and 24 through which the ends 25 and 26 of strap 10 are reeved. Vertical member 12 is provided with bends at points 29 and 30 to space vertical member 12 away from the body. Horizontal member 14 is provided with similar bends at points 31 and 32 for the same purpose. Although not shown in the drawings, vertical member 12 and horizonal member 14 can be provided with means for adjusting the length of each member so that a single brace can be adjusted to fit persons of various sizes. Such adjustment means are shown in U.S. Pat. No. 4,173,973 to Hendricks, issued Nov. 13, 1979, which patent is hereby incorporated by reference as part of the present disclosure.

Also included in back brace 11 is a back pad 33 which is a padded, generally rectangular plate curved to conform to the shape of the lumbar area of the back. Back pad 33 is provided with vertical slots 34 and 35, one located near each side of backpad 33. End 25 of back brace strap 10 is reeved through slot 34 and end 26 is reeved through slot 35 such that back brace strap 10 is located on the side of backpad 33 which is away from the body.

Referring in particular to FIGS. 2 and 3, there is shown the details of the construction of back brace strap 10. Back brace strap 10 includes a central core 38 including two layers of cotton canvas. Overlying central core 38 on both sides is a layer of absorbent terry-cloth 39. Core layers 38 and terry cloth layers 39 are secured together by alternating diagonal stitching 40 for substantially the full width of back brace strap 10. The edges of back brace strap 10 are finished with bias tape 41.

Diagonal stitching 40 serves not only to secure the various layers of back brace strap 10 together, but also serves to provide rigidity by substantially reducing shear deformation in the plane of the strap. This rigidity and resistance to shear deformation enables the strap to act as a cantelever to provide vertical support for back pad 33 as it is being put on by the patient and while it is being worn.

Back brace strap 10 is also provided with a widened middle portion 44 which is wider than the length of slots 34 and 35 in back pad 33. Widened middle portion 44 prevents back brace strap 10 from being diplaced longitudinally with respect to back pad 33, yet permits easy removal of strap 10 from back pad 33 for cleaning or replacement. Widened middle portion 44 also stiffens strap 10 in the middle to resist buckling of the strap and thereby provides further vertical support for back pad 33.

To assist in rapid adjustment and removal of strap 10, a Velcro multiple hook and loop type fastener is provided near ends 25 and 26 of strap 10. The Velcro is located on the side of strap 10 which is away from the body, with the hook portion 45 located nearest the ends 25 and 26 and the loop portion 46 located farther back from the ends on the same side of the strap. Each end 25 or 26 can be reeved through its respective slot 34 or 35, folded back and attached to the loop portion of the Velcro on the outside surface of the strap. Because the hook portion 45 is shorter than the loop portion 46, there is provided a range of adjustment for the length and tension of strap 10.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What I claim is:

1. In combination with a back brace of the type having an anterior frame configured to be applied to the anterior thoracic area of a person and a back pad configured to be applied to the lumbar area of a person and having strap means connected to said back pad and to said anterior frame for providing suitable tension therebetween, said back pad having vertical slots for receiving said strap means therethrough, the improvement comprising:

a strap constructed of a cloth-like material and having a middle portion, wherein said middle portion has a width dimension greater than the length dimension of either of said back pad slots, the middle portion of said strap freely overlying said back pad on a side opposite that side of said back pad which is applied to the lumbar area of the person, and being readily removable from said back pad, said strap having end portions each disposed through a respective slot of said back pad and secured to said anterior frame, whereby longitudinal displacement of said back pad with respect to said strap is precluded in normal use by said middle portion.

2. The improvement of claim 1, wherein said strap includes alternating diagonal stitching oriented diagonally with respect to the longitudinal dimension of said strap for substantially the full width of said strap, whereby said strap is stiffened against shear deformation.

3. The improvement of claim 2, wherein said strap is faced with an absorbent terry-cloth like material.

4. The improvement of claim 2, wherein each of the end portions of said strap has a multiple hook and loop type of fastener affixed thereto.

5. The improvement of claim 4, wherein said strap is faced with an absorbent terry-cloth like material.

* * * * *